United States Patent
Moore

(10) Patent No.: US 9,597,462 B2
(45) Date of Patent: Mar. 21, 2017

(54) CARTRIDGE HUB WITH ACTIVE VALVE

(71) Applicant: Sanofi-Aventis Deutschland GmbH, Frankfurt am Main (DE)

(72) Inventor: David Moore, Leicestershire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 14/369,138

(22) PCT Filed: Jan. 9, 2013

(86) PCT No.: PCT/EP2013/050297
§ 371 (c)(1),
(2) Date: Jun. 26, 2014

(87) PCT Pub. No.: WO2013/104665
PCT Pub. Date: Jul. 18, 2013

(65) Prior Publication Data
US 2014/0350460 A1    Nov. 27, 2014

(30) Foreign Application Priority Data

Jan. 9, 2012  (EP) .................................... 12150480

(51) Int. Cl.
*A61M 5/32*  (2006.01)
*A61M 5/168*  (2006.01)
(Continued)

(52) U.S. Cl.
CPC ...... *A61M 5/3294* (2013.01); *A61M 5/16827* (2013.01); *A61M 5/19* (2013.01);
(Continued)

(58) Field of Classification Search
CPC .. A61M 5/3294; A61M 5/19; A61M 5/14566; A61M 5/16827; A61M 5/16881; A61M 2039/229
See application file for complete search history.

(56) References Cited

U.S. PATENT DOCUMENTS 4,044,757 A * 8/1977 McWhorter ........ A61M 3/0262
                                                   600/432
4,381,778 A    5/1983 Kozam et al.
(Continued)

FOREIGN PATENT DOCUMENTS

CA    1185859         4/1985
JP    2010110572 A    5/2010
(Continued)

OTHER PUBLICATIONS

English Translation of First Office Action issued in Chinese Patent Application No. 201380012455.9 dated Jan. 6, 2016.
(Continued)

*Primary Examiner* — Andrew Gilbert
(74) *Attorney, Agent, or Firm* — McDonnell Boehnen Hulbert & Berghoff LLP

(57) ABSTRACT

The invention is related to a dispense interface for a drug delivery device for delivering at least two drug agents, wherein the dispense interface is configured to be coupled to a cartridge holder of the drug delivery device, wherein the cartridge holder is configured to hold at least two cartridges, wherein the dispense interface comprises at least two inlet channels, each comprising a fluid inlet opening, wherein each fluid inlet opening is configured to receive fluid from a respective cartridge of the at least two cartridges when the dispense interface is axially coupled to the cartridge holder, an outlet channel comprising a fluid outlet opening, a valve structure configured to be selectively moved into any one of a plurality of positions, wherein in at least one position the
(Continued)

valve structure selectively permits or prevents fluid flow from any of the at least two inlet channels to the outlet channel. The invention is further related to a drug delivery device for delivering at least two drug agents comprising a dispense interface of the aforementioned kind.

13 Claims, 10 Drawing Sheets

(51) Int. Cl.
    *A61M 5/19*     (2006.01)
    *A61M 5/20*     (2006.01)
    *A61M 5/145*     (2006.01)
    *A61M 5/34*     (2006.01)
    *A61M 5/24*     (2006.01)
    *A61M 5/31*     (2006.01)
    *A61M 5/142*     (2006.01)

(52) U.S. Cl.
    CPC ........... *A61M 5/20* (2013.01); *A61M 5/14244* (2013.01); *A61M 5/14566* (2013.01); *A61M 5/345* (2013.01); *A61M 2005/2407* (2013.01); *A61M 2005/2474* (2013.01); *A61M 2005/2496* (2013.01); *A61M 2005/3117* (2013.01); *A61M 2205/10* (2013.01); *A61M 2205/50* (2013.01); *F04C 2270/0421* (2013.01)

(56) References Cited

U.S. PATENT DOCUMENTS

| | | | | |
|---|---|---|---|---|
| 4,604,093 A * | 8/1986 | Brown | .............. | A61M 5/16827 137/625.11 |
| 4,610,666 A * | 9/1986 | Pizzino | ................... | A61M 5/19 604/191 |
| 5,147,323 A * | 9/1992 | Haber | ..................... | A61M 5/19 604/191 |
| 5,240,146 A * | 8/1993 | Smedley | ................. | A61M 5/19 222/137 |
| 5,286,258 A * | 2/1994 | Haber | ..................... | A61M 5/19 206/219 |
| 5,417,667 A * | 5/1995 | Tennican | ............ | A61M 5/1408 128/DIG. 12 |
| 5,478,323 A * | 12/1995 | Westwood | .............. | A61M 5/19 604/191 |
| 5,505,704 A * | 4/1996 | Pawelka | ................. | A61M 5/19 604/191 |
| 6,884,232 B1 * | 4/2005 | Hagmann | ........ | A61B 17/00491 604/191 |
| 6,921,381 B2 * | 7/2005 | Spero | ............... | A61B 17/00491 604/82 |
| 2011/0282381 A1 * | 11/2011 | Cronin | ............... | A61B 10/0275 606/213 |
| 2015/0157797 A1 * | 6/2015 | Eggert | .................... | A61M 5/19 604/506 |
| 2015/0202425 A1 * | 7/2015 | Yamamoto | ............ | A61M 5/007 600/432 |
| 2015/0320942 A1 * | 11/2015 | Laugere | .............. | A61M 5/1407 604/506 |

FOREIGN PATENT DOCUMENTS

| | | |
|---|---|---|
| WO | 03039375 A2 | 5/2003 |
| WO | 2010/051205 A1 | 5/2010 |

OTHER PUBLICATIONS

English Translation of Office Action issued in Japanese Patent Application No. 2014-550724 dated Sep. 27, 2016.

* cited by examiner

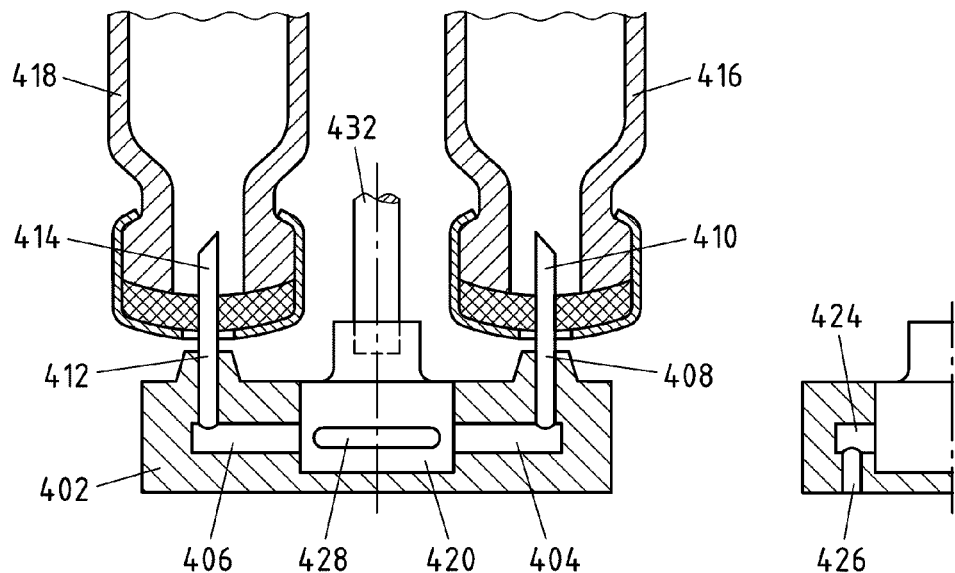
Fig.12
Fig.13
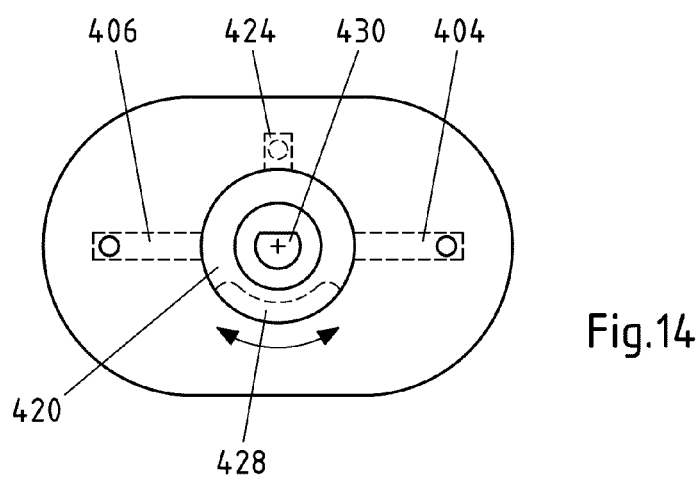
Fig.14
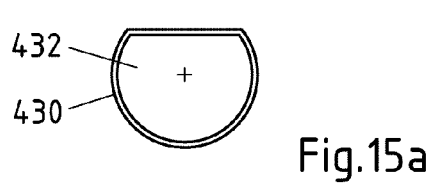
Fig.15a
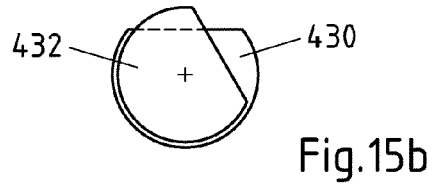
Fig.15b

CARTRIDGE HUB WITH ACTIVE VALVE

CROSS REFERENCE TO RELATED APPLICATIONS

The present application is a U.S. National Phase Application pursuant to 35 U.S.C. §371 of International Application No. PCT/EP2013/050297 filed Jan. 9, 2013, which claims priority to European Patent Application No. 12150480.7 filed Jan. 9, 2012. The entire disclosure contents of these applications are herewith incorporated by reference into the present application.

FIELD OF INVENTION

The present patent application relates a dispense interface for a drug delivery device for delivering at least two drug agents and to a drug delivery device with such a dispense interface.

BACKGROUND

A drug delivery device is a medical device for delivering drug agents. A charge of a drug agent to be delivered usually comes in a cartridge, and the drug delivery device here may therefore be configured to accommodate at least two cartridges. Each cartridge forms a separate reservoir of the drug agent. When the drug delivery device only has a single injection needle to deliver the drug agents, a valve construction may be necessary to control the flow of the drug agents from their respective cartridges to the injection needle.

There are various medical devices for delivering at least two drug agents from separate reservoirs. Such drug agents may comprise a first and a second medicament. Such a medical device includes a dose setting mechanism for delivering the drug agent(s) automatically or manually by the user.

SUMMARY

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in one or more multiple dose reservoirs, containers or packages containing independent (single drug compound) or pre-mixed (co-formulated multiple drug compounds) drug agent(s).

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

A drug delivery device, described in more detail hereinafter, comprises a mechanism implementing a valve functionality for regulating the flow of each drug agent from its respective cartridge through a dispense interface of the drug delivery device to the injection needle and in particular enabling a selective discharge of the drug agents.

One way of implementing the valve functionality that is required to enable a selective discharge of the primary, secondary and potential further medicaments is to employ elastomeric valves. These valves may, for example, comprise a membrane that deflects or inverts and permits fluid flow from the respective cartridge once the pressure applied on the fluid in the cartridge and further transmitted to the membrane exceeds a certain level.

The pressure is applied to the fluid in the cartridge by advancing a bung within the cartridge by using a plunger in the cartridge holder. Taken as a function of the extension of the plunger, the opening and closing behavior of the membrane valve is highly variable. That is, with repeated fluid discharge operations the initial opening of the membrane may happen at different fluid pressures caused by the plunger. If the bung in the cartridge shows elastic properties, the plunger may have already advanced and compressed the bung when the fluidic pressure opens the valve. Thus, the advancement of the plunger does not directly correlate to the amount of medicament expelled from the cartridge at all times during the injection process. Similarly, the closing behavior of the membrane valve may be irregular, whereby a precise dosage of the discharged medicament becomes difficult. Moreover, these deviations from the desired discharge amount may be hard to detect or to predict.

Thus it is an object of the invention to provide a dispense interface in which the precision of the medicament dosage is improved.

This object is solved by a dispense interface for a drug delivery device for delivering at least two drug agents, wherein the dispense interface is configured to be coupled to the drug delivery device, for example axially coupled, e.g. to a cartridge holder of the drug delivery device, wherein the cartridge holder is configured to hold at least two cartridges, wherein the dispense interface comprises at least two inlet channels, each comprising a fluid inlet opening configured to receive fluid from a respective cartridge of the at least two cartridges when the dispense interface is axially coupled to the cartridge holder, an outlet channel comprising a fluid outlet opening, a valve structure configured to be selectively moved into any one of a plurality of positions, wherein in at least one position the valve structure selectively permits or prevents fluid flow from any of the at least two inlet channels to the outlet channel.

By using an active valve control mechanism with a valve structure that can be varied in its position, the operation of the valves may be better controlled. Thereby the time of opening as well as the time of closing of the valve and therefore also the dosage may be adjusted more precisely. Further, the valve may be opened without having to build up fluid pressure in the respective cartridge. It also enables to detect the bung by actively closing the cartridge hub valves and advancing the plungers. In addition, leakage can be completely avoided in an actively closed valve in contrast to a membrane valve. The solution according to the invention also avoids the back pressure that is present when the membrane valve is open. This back pressure is hard to calculate exactly and affects the passage of the drug agents, but does not arise when an actively controlled valve is used.

Each cartridge may hold a respective primary, secondary or further medicament to be injected by the drug delivery device. The fluid outlet opening may further lead to a needle assembly which may be attached to the dispense interface at the distal end of the dispense interface, which needle assembly may comprise or connect to injection needles. The valve structure is a mechanical entity which can assume a number of positions. For each fluid inlet opening, there is at least one associated position of the valve structure in which the valve structure permits fluid flow from that fluid inlet opening to the outlet channel and blocks fluid flow from all the other fluid inlet openings. There may also be at least one position of the valve structure in which fluid flow from all the fluid inlet openings is blocked.

Each fluid inlet opening of the at least two inlet channels is arranged at a proximal end of the dispense interface. Thereby, when the dispense interface is axially coupled to a cartridge holder at the proximal end of the dispense interface, each cartridge is connected to its associated fluid inlet opening.

Further the fluid outlet opening is arranged at a distal end of the dispense interface. Thereby the fluid outlet opening is connected to a fluid channel of the needle assembly when that needle assembly is attached to the dispense interface at the distal end of the dispense interface.

In a preferred embodiment, the valve structure is a rotating valve configured to move into any one of a plurality of positions by a rotating movement. The rotating movement of the valve structure may be a rotation around an axis that is parallel or identical to the longitudinal axis of the dispense interface. In this case the feature of the valve structure that selectively enables fluid flow from the respective fluid inlet opening to the outlet channel may be arranged on a lateral surface of the valve structure with respect to the axis of rotation of the valve structure.

In a further preferred embodiment, the valve structure comprises a fluid transfer pathway on a lateral surface of the valve structure, which fluid transfer pathway is configured to permit, in at least one of the plurality of positions, fluid flow from any one inlet channel to the outlet channel and to prevent fluid flow from the other inlet channels to the outlet channel. The lateral surface of the valve structure is a lateral surface with respect to a longitudinal axis of the valve structure.

In yet another preferred embodiment, the fluid transfer pathway is a groove. A groove in this context is a notch on a surface of the valve structure. Using a groove as a fluid transfer pathway has the advantage of allowing a less complicated production of the valve structure. In particular no fluid transfer pathway in the shape of a tunnel is necessary.

In a still further preferred embodiment, the valve structure comprises a coupling structure configured to engage a valve coupling feature of the chassis or cartridge holder when the dispense interface is coupled to the chassis or cartridge holder. For this purpose the valve structure is in an engaging position of the plurality of positions. The coupling structure of the valve structure may protrude or be otherwise accessible in a proximal direction of the dispense interface. The coupling structure may be an opening with an asymmetric cross-section. The coupling structure may also be an opening with a cross-section which is not symmetric with rotation. On the other hand the valve coupling feature may be a protrusion with a corresponding cross-section. Alternatively, the coupling structure may comprise the protrusion and the valve coupling feature the opening.

Because of the lack of rotational symmetry and the congruence of the cross-section of the opening and protrusion and because the valve coupling feature may be in a predetermined orientation when the cartridge holder is coupled to the dispense interface, it may only be possible to couple the chassis or cartridge holder to the dispense interface in some or even only one position of the valve structure. Such a position is an engaging position of the valve structure. An engaging position of the valve structure may correspond to a position in which fluid flow from one of the at least two inlet channels to the outlet channel is permitted. An engaging position of the valve structure may also correspond to a position in which fluid flow from all of the inlet channels to the outlet channel is blocked.

In a preferred embodiment, the coupling structure is configured to block the engaging of the valve coupling feature of the cartridge holder, thereby preventing or blocking coupling of the dispense interface to the cartridge holder, when the valve structure is in at least one blocking position of the plurality of positions. A blocking position of the valve structure may correspond to a position in which fluid flow from one of the at least two inlet channels to the outlet channel is permitted. A blocking position of the valve structure may also correspond to a position in which fluid flow from all of the inlet channels to the outlet channel is blocked. By the features of this embodiment, the coupling of the dispense interface to the cartridge holder may only be permitted in certain defined states of the dispense interface. In particular, this permits moving the valve structure into a position before or after injection of the medicaments that prevents reuse of the dispense interface.

In another preferred embodiment, the coupling structure is a notch and the valve coupling feature is a protrusion. Thereby the coupling mechanism between the dispense interface and the cartridge hub is achieved by simple and robust mechanical means.

In a further preferred embodiment, the coupling structure is configured to enable moving the valve structure into any one of the plurality of positions by the chassis or cartridge holder when the coupling structure is engaged to the valve coupling feature. The coupling structure may for example be a protrusion of the valve structure along the longitudinal axis of the valve structure. The valve coupling feature of the cartridge holder may for example be arranged on a pivot of the chassis or cartridge holder. By rotating the pivot, the chassis or cartridge holder—when coupled to the dispense interface—can rotate the valve structure in a similar way or in the same way that a screwdriver rotates a screw, thereby being able to move the valve structure into any of the plurality of positions. Since the discharge of the fluids from the cartridges is also enacted by the chassis or cartridge holder or a unit linked to the chassis or cartridge holder, control of the valve structure by the chassis or cartridge holder permits close control synchronization between the fluid discharge from the cartridges and the operation of the valve structure.

In a still further preferred embodiment, the dispense interface comprises a valve driving construction configured to selectively move the valve structure into any of the plurality of positions. The valve driving construction may comprise actuators. The actuators may be electrically controlled.

In a preferred embodiment, the valve driving construction comprises an electrical motor configured to move the valve structure. The electrical motor may be configured to be powered by electricity received from the chassis or cartridge holder when the dispense interface is coupled to the chassis or cartridge holder. Thereby an electronic control of the valve operation is enabled, rather than a manual control of the valve operation.

In another preferred embodiment, the valve driving construction comprises at least one electric contact configured to receive electrical signals from the drug delivery device, for example through or from the cartridge holder or directly from the chassis of the drug delivery device. The chassis or cartridge holder may comprise corresponding electronic pins configured to transmit the control signals to the valve driving construction in the dispense interface. The electrical signals may comprise control signals. The electrical signals may also comprise an electrical power supply signal to power the electrical motor. The electrical power supply signal may be a DC electrical signal or an AC electrical signal. The electrical signal may further comprise pulse-width or otherwise modulated signals. In a further preferred embodiment, the electrical motor is configured to move the valve structure based on the electrical signals received from the chassis or cartridge holder.

In another preferred embodiment, the valve driving construction comprises at least one electric contact configured to receive electrical signals from the chassis or cartridge holder, and the chassis or cartridge holder may comprise corresponding electronic pins configured to transmit the control signals to the valve driving construction in the dispense interface. The valves are electronically powered valves. The electric signals may comprise control signals for the electronically powered valves. There may be a control signal for each valve. For example, the valve is in the open position when the control signal is a "high" voltage (for example 5 V), and the valve is in the closed position when the control signal is a "low" voltage, e.g. zero volt.

In a preferred embodiment, the coupling feature locks the dispense interface to the device, so that removal can be prevented for example during dispense or bung detect. For example, the valve structure comprises a propelling feature configured to engage a linking arrangement of the cartridge holder and configured to pull the cartridge holder towards the dispense interface when the valve structure is moved into an attachment position of the plurality of positions and further configured to push the cartridge holder away from the dispense interface when the valve structure is moved into a detachment position of the plurality of positions. Thereby the coupling of the dispense interface to the cartridge holder does not solely rely on a manual coupling by the user. Instead, the user need only ensure correct positioning, whereas the mechanical completion and tightening of the coupling is enacted by an automatic mechanism. This also helps further ensure that a coupling of sufficient quality is enacted prior to the injection of the medicaments to be delivered.

In a preferred embodiment, the propelling feature is a groove and the linking arrangement is a ridge.

In another preferred embodiment, the linking arrangement is a screw threaded nut and the propelling feature is a (short) length of a screw thread mounted axially upon a shaft. In this embodiment, attachment of the dispense interface to the chassis or cartridge holder is made by turning the shaft in a first direction and thus screwing it into the screw threaded nut, for example for a predefined number of rotations, or until it abuts an end surface in the nut. Further turning the shaft in the first direction moves or rotates the valve. By further rotation of the shaft in the first direction, the valve can be moved from a closed position into an open position, or the valve can be moved from an open position to a closed position. For example, for a first 90 degree turn in the first direction, the valve is moved from an open position to a closed position, and for a (subsequent) second 90 degree turn in the first direction, the valve is moved from the closed position to an open position again. Additional 90 degree turns in the first direction will open and close the valve again. Turning the shaft in the opposite direction will unscrew the screw thread from the screw threaded nut again and thus detach the dispense interface from the chassis or cartridge holder.

The object of the invention is further solved by a drug delivery device comprising a dispense interface according to the invention.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which:

FIG. 12 illustrates a cross-sectional view of a further dispense interface according to the invention with cartridges connected to and a peg engaging the dispense interface;

FIG. 13 illustrates a lateral cross-sectional view of the dispense interface according to the invention illustrated in FIG. 12;

FIG. 14 illustrates a longitudinal cross-sectional view of the dispense interface according to the invention illustrated in FIG. 12 and FIG. 13; and FIGS. 15a and 15b illustrate a fitting alignment and a not-fitting alignment of the notch of a valve structure and the protrusion of a cartridge holder.

DETAILED DESCRIPTION

Figure 1:
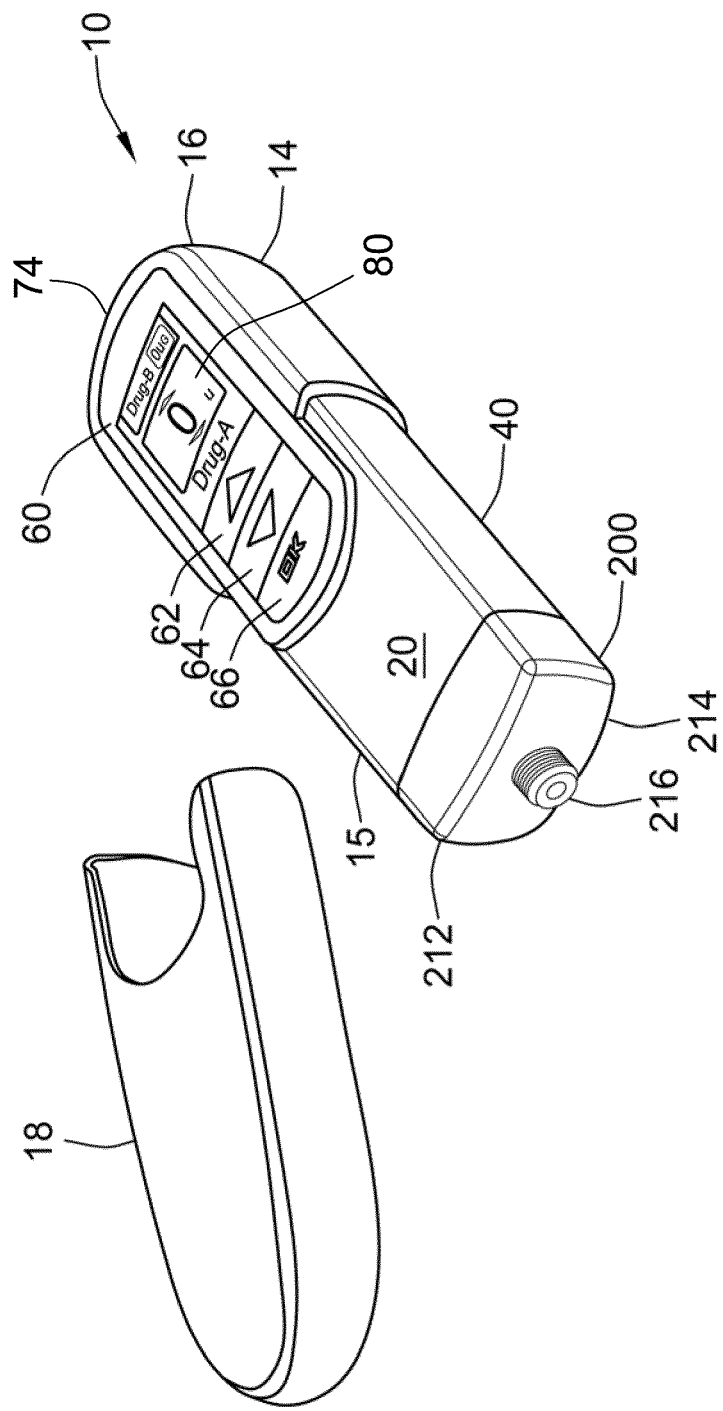
FIG. 1 illustrates a perspective view of a delivery device with an end cap of the device removed.
Figure 2:
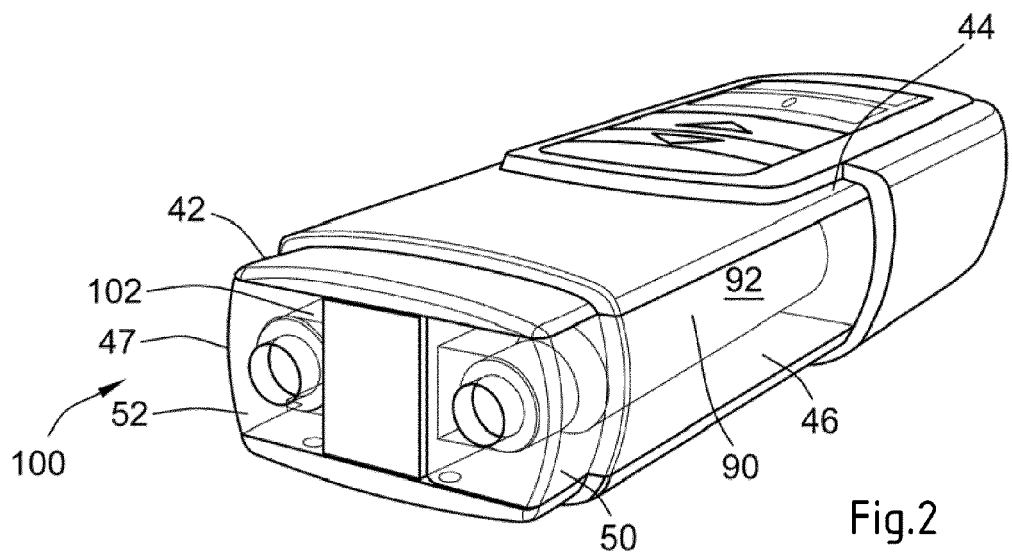
FIG. 2 illustrates a perspective view of the delivery device distal end showing the cartridge.

Before describing the embodiment, of the invention, an exemplary embodiment of a drug delivery device is explained, which can be used for applying the invention. The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user with certain device information, preferably information relating to the medicaments contained within the cartridge holder 40. For example, the user is provided with certain information relating to both the primary medicament (Drug A) and the secondary medicament (Drug B).

Figure 3:
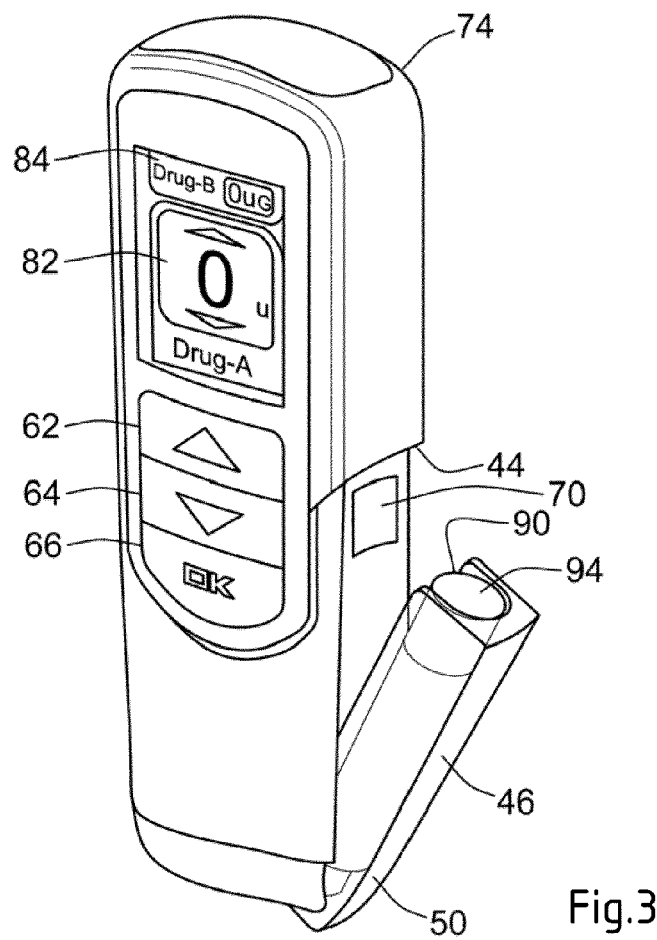
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
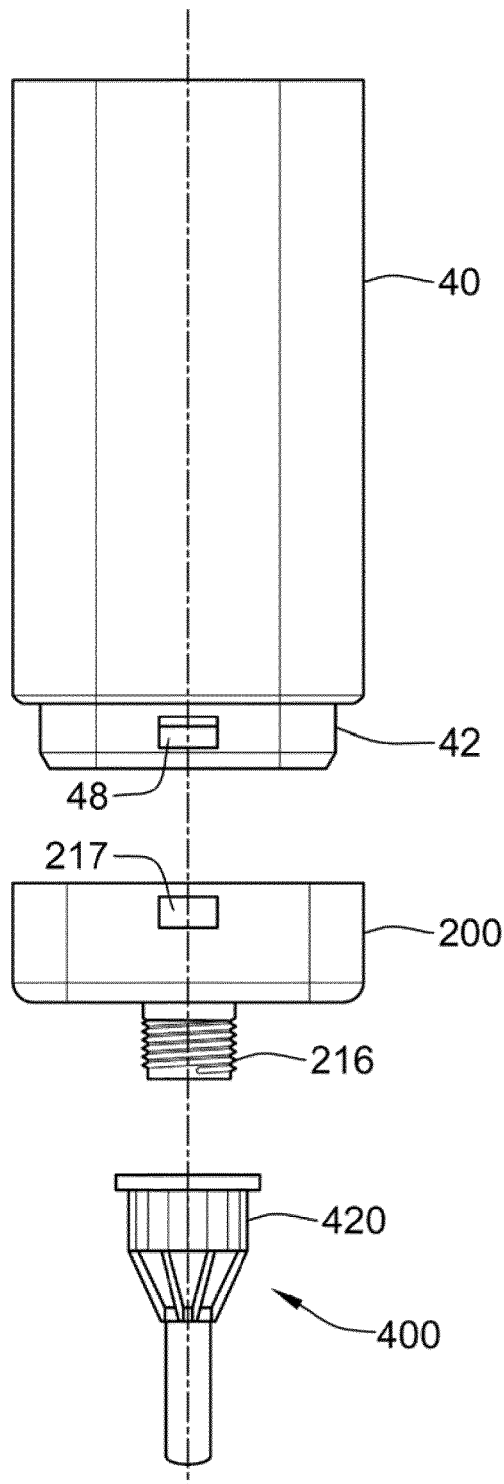
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
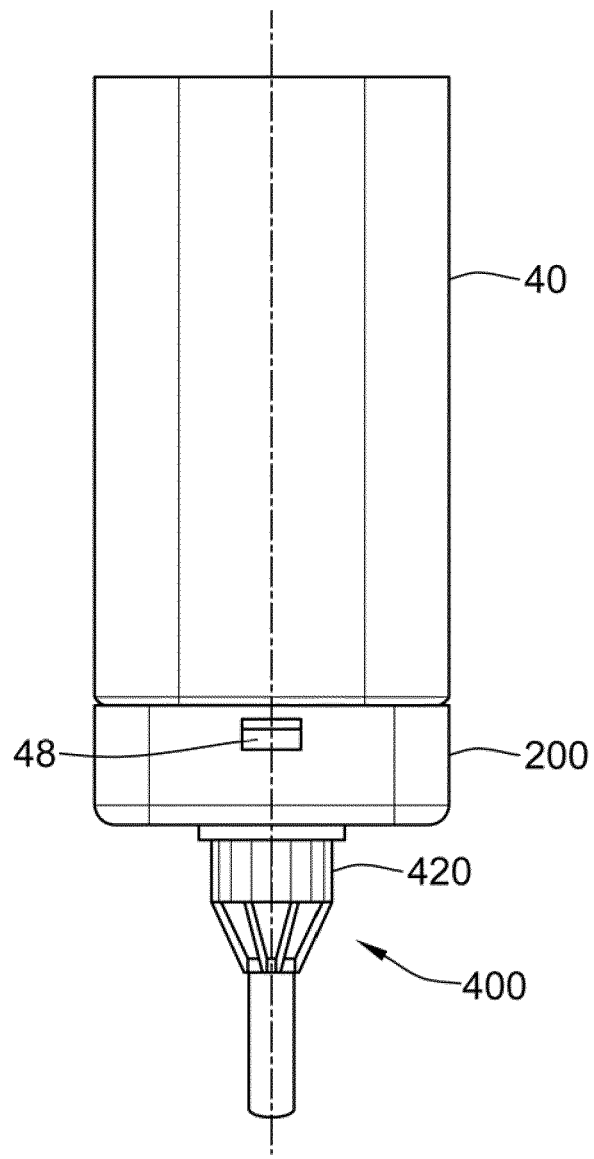
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
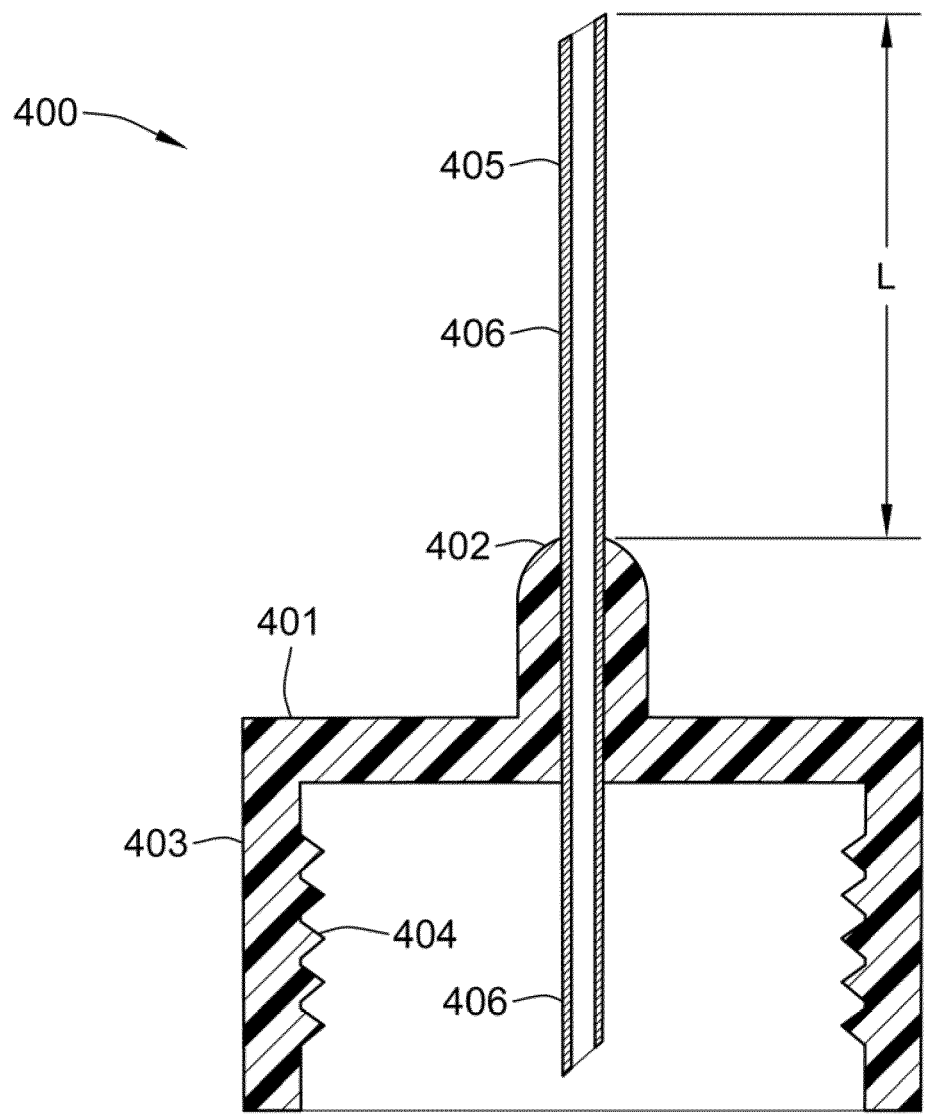
FIG. 6 illustrates one arrangement of a needle assembly that may be mounted on a distal end of the delivery device.
Figure 7:
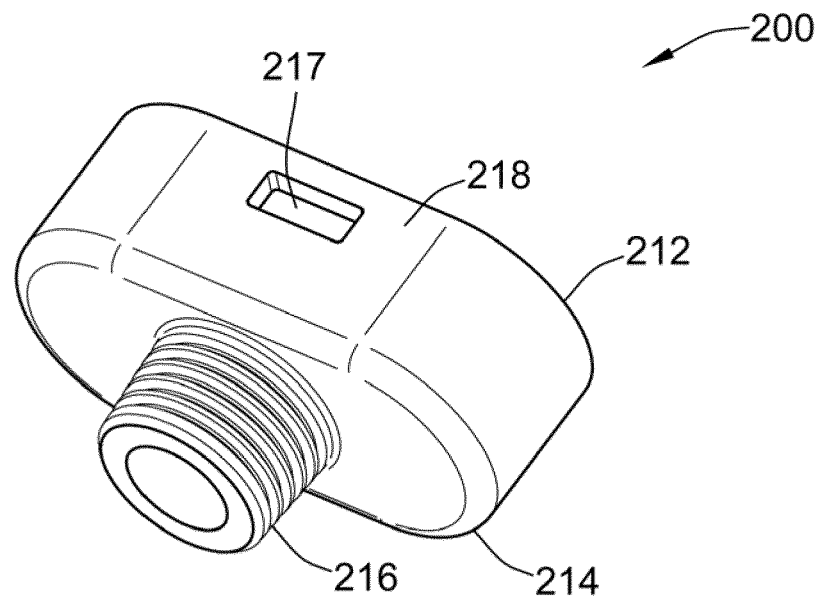
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element and a sleeve 403. Along an inner wall of this sleeve 403, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIGS. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
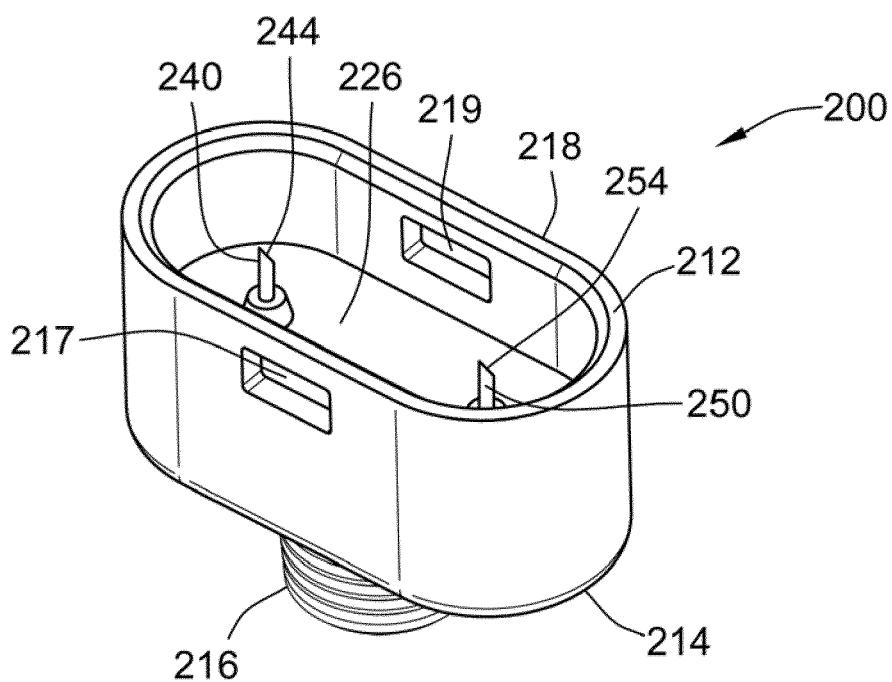
FIG. 8 illustrates another perspective view of the dispense interface illustrated in FIG. 4.
Figure 9:
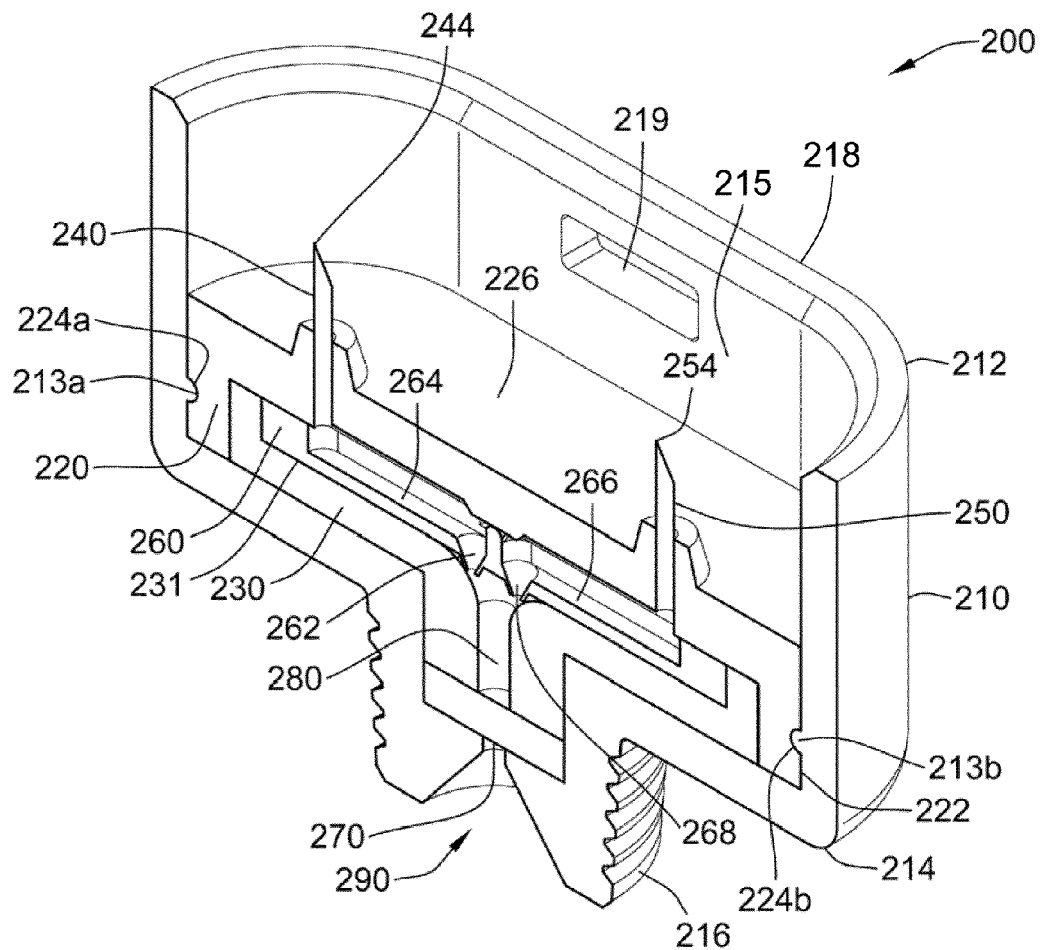
FIG. 9 illustrates a cross-sectional view of the dispense interface illustrated in FIG. 4.
Figure 10:
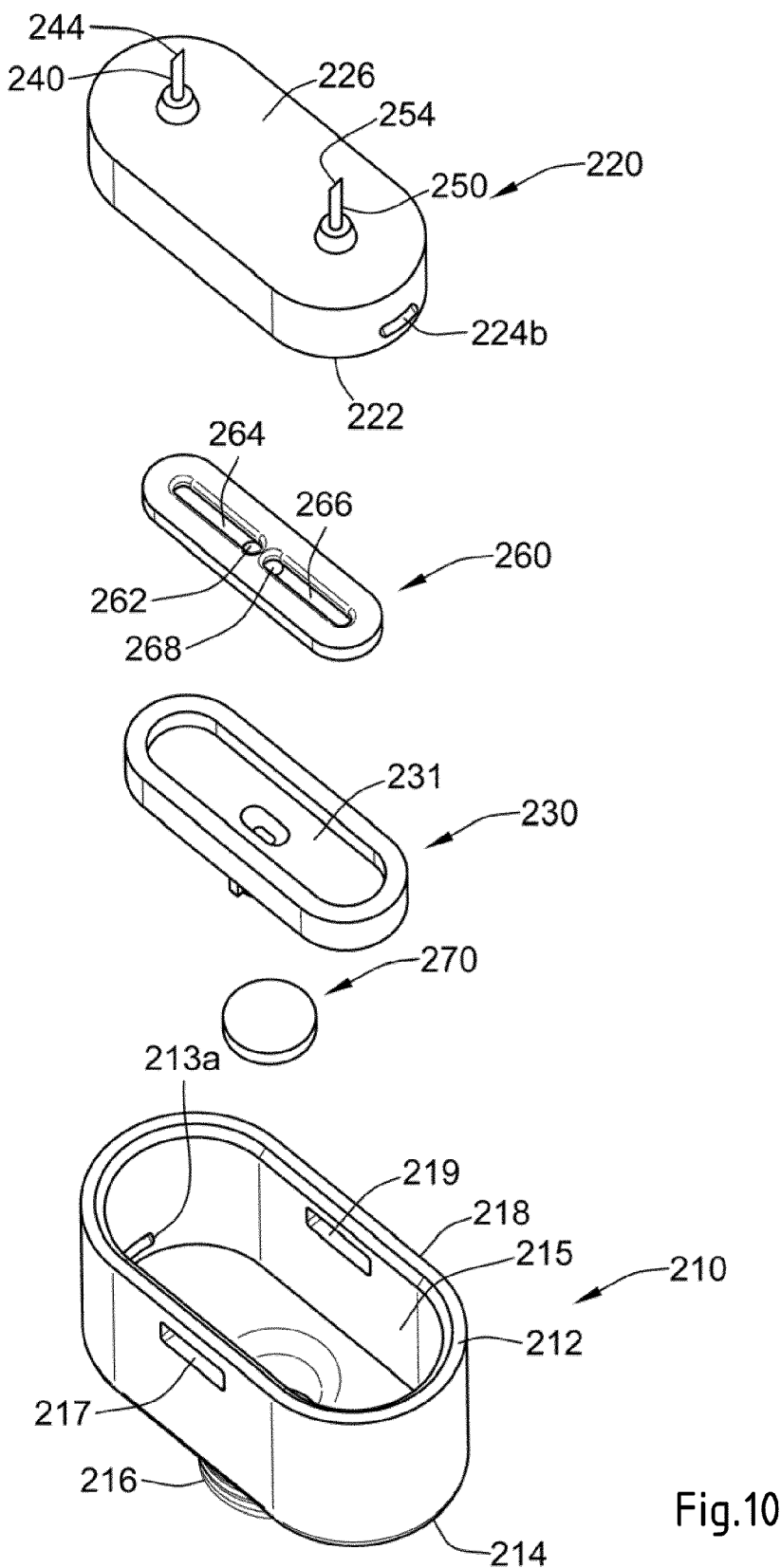
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
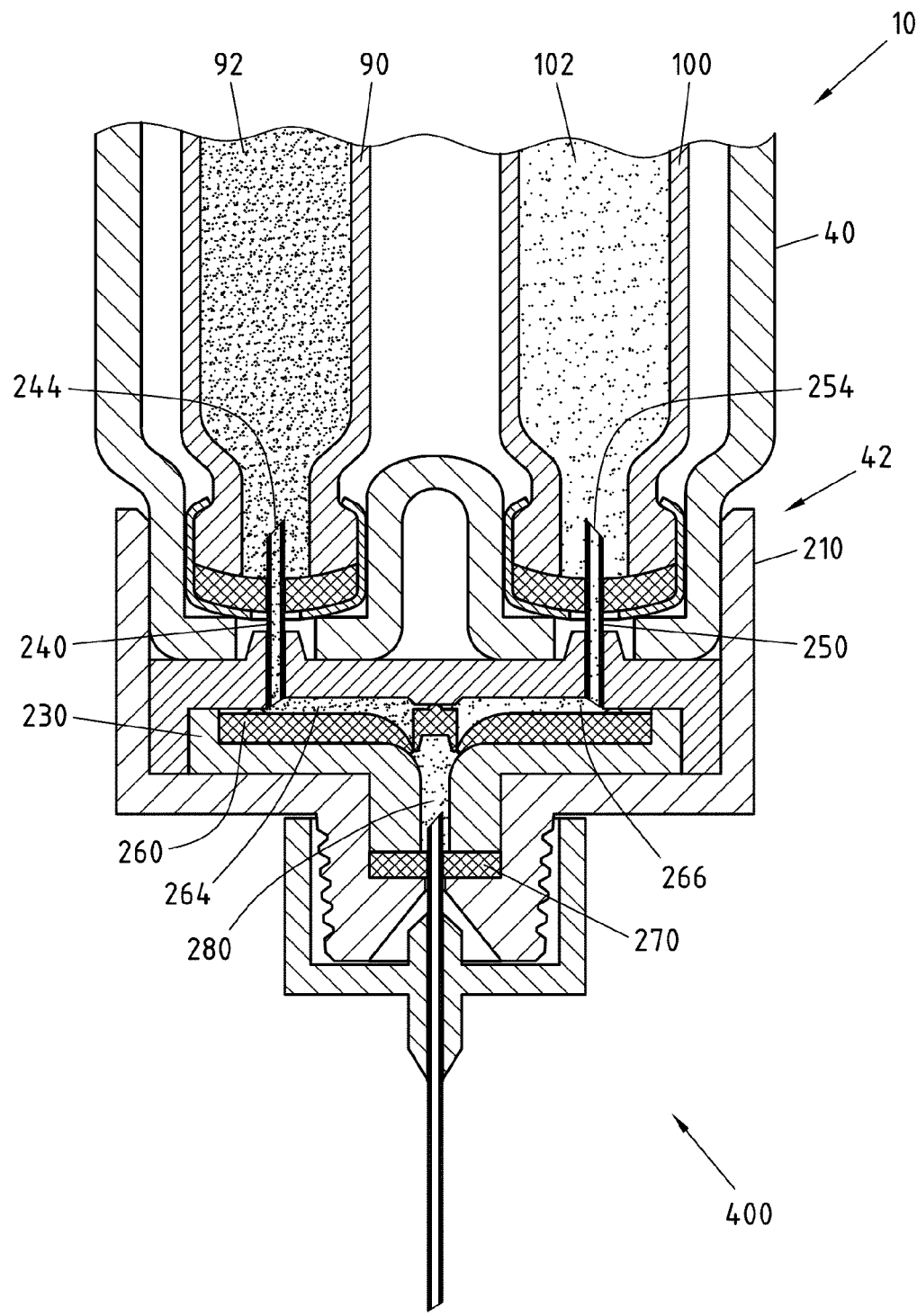
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Referring now to FIG. 12-14, there is illustrated an embodiment of the dispense interface according to the present invention. The dispense interface 402 is axially coupled to chassis or a cartridge holder (not illustrated in its entirety) of the drug delivery device. The dispense interface 402 comprises a first inlet channel 404 and a second inlet channel 406. The first inlet channel 404 comprises a first fluid inlet opening 408, in which a first needle 410 is arranged. Similarly, the second inlet channel 406 comprises a second fluid inlet opening 412, in which a second needle 414 is arranged. The first needle 410 is in fluid communication with a first cartridge 416 filled with a primary medicament. The second needle 414 is in fluid communication with a second cartridge 418 filled with a secondary medicament.

Further, the dispense interface 402 also comprises a third channel, which is an outlet channel 424 with a fluid outlet opening 426. The fluid outlet opening leads to a needle assembly with an injection needle (not shown).

The dispense interface 402 further comprises a valve structure 420, which is here a rotating valve, arranged along a central longitudinal axis of the dispense interface 402. This valve 420 provides a fluid transfer pathway 428. In one of two "open" positions, the rotating valve 420 enables a fluid connection between the first inlet channel 404 and the outlet channel 424 or between the second inlet channel 406 and the outlet channel 424. In a closing position, illustrated in FIG. 14, fluid flow between the inlet channels 404, 406 and the outlet channel 424 is blocked.

The rotating valve 420 has a coupling structure, which in the present case is a notch 430. The notch 430 protrudes from the dispense interface 402 in a proximal direction of the dispense interface 402, i.e. facing the cartridge holder. This notch 430 is configured for insertion of a valve coupling feature of the cartridge holder, which in general may be a protrusion. In the particular case illustrated, the protrusion is a peg 432 of the chassis or cartridge holder. Notch 430 and peg 432 share the same cross-section. Because of the shape of the cross-section, illustrated in FIG. 14 and FIGS. 15a and 15b, the peg 432 can only be inserted into the notch 430 when the orientation of the notch 430 and the peg 432 matches. Thereby a coupling of the dispense interface 430 and the cartridge holder is prevented when there is no such match.

When the peg 432 is inserted into the notch 430, the operation of the rotating valve 420 can be controlled by the peg 432. Therefore the rotating valve 420 can for example be controlled by further control logic implemented outside the dispense interface 402, for example by the microprocessor control unit of the main body 14.

A typical operation of the dispense interface 402 shall now be described. The cartridge holder with two cartridges 416, 418 is ready to be coupled to the dispense interface 402. The peg 432 of the cartridge holder is oriented identically to the notch 430, thereby enabling the coupling, during which the peg 432 is inserted into the notch 430, thereby engaging the notch 430.

In the initial orientation, shown in FIG. 14 and FIG. 15a, the orientation of the rotating valve 420 blocks all fluid flow between the inlet channels 404, 406 and the outlet channel 424.

As part of the drug delivery procedure, the primary medicament from the first cartridge 416 is to be injected. To that end, the peg 432 turns the rotating valve 420 in an anti-clockwise direction until the transfer pathway 428 creates a fluid connection between the first inlet channel 404 and the outlet channel 424. Now the bung in the first cartridge 416 advances, thereby discharging the primary medicament from the first cartridge 416 via the fluid outlet 426 to the injection needle. The bung advances in the first cartridge 416 until the desired amount of primary medicament has been injected.

Once the injection of the primary medicament is complete, the peg 432 turns the rotating valve 420 further still in an anti-clockwise direction until the transfer pathway 428 creates a fluid connection between the second inlet channel 406 and the outlet channel 424.

Then the bung in the second cartridge 418 advances, discharging the secondary medicament from the second cartridge 418 via the fluid outlet 426 to the injection needle.

Once the injection of the secondary medicament is complete, the peg 432 turns the rotating valve 420 to a position in which the orientation of the notch 430 is not identical to the orientation of the notch 430 in the initial state, i.e. different from the orientation shown in FIG. 14. An example would be a position of the peg 432 as shown in FIG. 15b. This position of the rotating valve 420 may also be a position in which the transfer pathway 428 blocks fluid communication between the inlet channels 404, 406 and the outlet channel 424.

Alternatively to moving the peg 432 to a position in which the orientation of the notch 430 is not identical to the initial state only after injection, the peg 432 can be moved to such a position already directly after attachment of the dispense interface to the chassis or cartridge holder. After each injection, the peg 432 then moves the notch 430 to this position again.

After the dispense interface is removed, the peg 432 moves back into the initial position for attachment of a new dispense interface.

Removal of the used dispense interface may be detected by a sensor or switch in the cartridge holder, the chassis of the drug delivery device, or even in the peg 432. The sensor or switch may be triggered by a corresponding mechanical structure (e.g. a wall or a surface) of the dispense interface.

Thus, when the dispense interface 402 is removed from the cartridge holder or chassis of the drug delivery device and a re-coupling of the used dispense interface 402 is attempted, the coupling of the used dispense interface 402 to the cartridge holder or chassis will not succeed because the notch 430 of the used dispense interface 402 will not be able to engage the peg 432 with a different alignment. As the peg 432 has moved back into the initial position, only a new, unused cartridge hub can be attached. Thereby reuse of the dispense interface 402 is prevented.

Attaching and removing the dispense interface to the drug delivery device may therefore comprise the following steps, provided that the peg 432 of the drug delivery device is in the initial position for attachment of a new dispense interface:

- detecting attachment of a new dispense interface, for example by a switch or sensor;
- optionally, locking the dispense interface to the chassis or cartridge holder;
- operating the valve in the cartridge holder through the peg 432, i.e. opening or closing one or more fluid paths in the valve;
- moving the valve to a closed position (i.e. a position in which all fluid paths are closed) different from the initial position;
- detecting removal of the dispense interface, for example by the switch or sensor; and
- moving/turning the peg 432 back into the initial position for attachment of a new dispense interface.

Alternatively, attaching and removing the dispense interface to the drug delivery device may comprise the following steps. Here, the valve is moved to a different position directly after attachment of the dispense interface:

- detecting attachment of a new dispense interface, for example by a switch or sensor;
- optionally, locking the dispense interface to the chassis or cartridge holder;
- moving the valve to a closed position different from the initial position by rotation of peg 432;
- operating the valve in the cartridge holder through the peg 432, i.e. opening or closing one or more fluid paths in the valve;
- moving the valve to the closed position different from the initial position (this may be the same closed position as in the step above);
- detecting removal of the dispense interface, for example by the switch or sensor; and
- moving/turning the peg 432 back into the initial position for attachment of a new dispense interface.

The step of detecting removal of the dispense interface may comprise detection of an eject button or switch that may be operated by a user. After the detection of the eject button press, the dispense interface may be unlocked, if it was previously locked to the device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for a drug delivery device for delivering at least two drug agents,
   wherein the dispense interface is configured to be axially coupled to a cartridge holder of the drug delivery device,
   wherein the cartridge holder is configured to hold at least two cartridges,
   wherein the dispense interface comprises:
   at least two inlet channels, each comprising a fluid inlet opening configured to receive fluid from a respective cartridge of the at least two cartridges when the dispense interface is axially coupled to the cartridge holder;
   an outlet channel comprising a fluid outlet opening; and
   a valve structure configured to be selectively moved into any one of a plurality of positions when the dispense interface is coupled to the cartridge holder, wherein in at least one position the valve structure selectively permits or prevents fluid flow from any of the at least two inlet channels to the outlet channel,
   wherein the valve structure comprises a coupling structure configured to engage a valve coupling feature of the cartridge holder when the dispense interface is coupled to the cartridge holder, and
   wherein, when the valve structure is in at least one blocking position of the plurality of positions, the coupling structure is configured to block the engaging of the valve coupling feature of the cartridge holder, thereby preventing coupling of the dispense interface to the cartridge holder.

2. The dispense interface of claim 1, wherein:
   the valve structure is a rotating valve configured to move into any one of a plurality of positions by a rotating movement.

3. The dispense interface of claim 1, wherein:
   the valve structure comprises a fluid transfer pathway on a lateral surface of the valve structure,
   which fluid transfer pathway is configured to permit, in at least one of the plurality of positions, fluid flow from any one inlet channel to the outlet channel and to prevent fluid flow from the other inlet channels to the outlet channel.

4. The dispense interface of claim 3, wherein:
   the fluid transfer pathway is a groove.

5. The dispense interface of claim 1, wherein:
   the coupling structure is a notch and the valve coupling feature is a protrusion.

6. The dispense interface of claim 1, wherein:
   the coupling structure is configured to enable moving the valve structure into any one of the plurality of positions by the cartridge holder when the coupling structure is engaged to the valve coupling feature.

7. The dispense interface of claim 1, comprising:
   a valve driving construction configured to selectively move the valve structure into any of the plurality of positions.

8. The dispense interface of claim 7, wherein:
   the valve driving construction comprises an electrical motor configured to move the valve structure.

9. The dispense interface of claim 8, wherein:
   the valve driving construction comprises at least one electric contact configured to receive electrical signals from the cartridge holder.

10. The dispense interface of claim 9, wherein:
    the electrical motor is configured to move the valve structure based on the electrical signals received from the cartridge holder.

11. The dispense interface of claim 1, wherein:
    the valve structure comprises a propelling feature
    configured to engage a linking arrangement of the cartridge holder;
    configured to pull the cartridge holder towards the dispense interface when the valve structure is moved into an attachment position of the plurality of positions; and
    configured to push the cartridge holder away from the dispense interface when the valve structure is moved into a detachment position of the plurality of positions.

12. The dispense interface of claim 11, wherein:
    the propelling feature is a groove and the linking arrangement is a ridge.

13. Drug delivery device for delivering at least two drug agents comprising a dispense interface according to claim 1.

* * * * *